(12) United States Patent
Mosharrafa

(10) Patent No.: US 11,065,075 B2
(45) Date of Patent: Jul. 20, 2021

(54) SYSTEMS AND METHODS FOR A TISSUE EXPANDER

(71) Applicant: Reconstructive Technologies, LLC, Phoenix, AZ (US)

(72) Inventor: Tamir Mostafa Mosharrafa, Paradise Valley, AZ (US)

(73) Assignee: Reconstructive Technologies, LLC, Phoenix, AZ (US)

( * ) Notice: Subject to any disclaimer, the term of this patent is extended or adjusted under 35 U.S.C. 154(b) by 0 days.

(21) Appl. No.: 16/879,674

(22) Filed: May 20, 2020

(65) Prior Publication Data
US 2020/0367988 A1 Nov. 26, 2020

Related U.S. Application Data

(60) Provisional application No. 62/850,287, filed on May 20, 2019, provisional application No. 62/987,301, filed on Mar. 9, 2020.

(51) Int. Cl.
*A61M 29/02* (2006.01)
*A61F 2/12* (2006.01)
*A61B 90/00* (2016.01)

(52) U.S. Cl.
CPC .............. *A61B 90/02* (2016.02); *A61F 2/12* (2013.01); *A61M 29/02* (2013.01)

(58) Field of Classification Search
CPC ............. A61B 90/02; A61F 2/0063; A61F 2002/0068; A61F 2/12; A61M 29/02
USPC ......................................... 606/151, 190–198
See application file for complete search history.

(56) References Cited

U.S. PATENT DOCUMENTS

| | | | |
|---|---|---|---|
| 4,264,990 A | 5/1981 | Hamas | |
| 4,902,294 A * | 2/1990 | Gosserez | A61F 2/12 623/8 |
| 5,133,753 A | 7/1992 | Bark et al. | |
| 6,666,893 B2 | 12/2003 | Burg et al. | |
| 9,399,122 B2 | 7/2016 | Mosharrafa et al. | |
| 9,713,524 B2 | 7/2017 | Glicksman | |
| 10,039,633 B2 | 8/2018 | Ansorge et al. | |
| 2003/0093151 A1* | 5/2003 | Zhang | A61F 2/12 623/8 |

(Continued)

FOREIGN PATENT DOCUMENTS

EP 3348234 7/2018

*Primary Examiner* — Kathleen S Holwerda
(74) *Attorney, Agent, or Firm* — The Deneau Law Firm, PLLC

(57) ABSTRACT

Systems and methods for an extended tissue expander according to various aspects of the present technology may function in conjunction with a graft material for temporary implantation into a patient to form a pocket for a permanent implant. Systems and methods may comprise an extended tissue expander comprising an extension portion that may be integral to a posterior section of a shell of the extended tissue expander, wherein the extension portion extends from the posterior section forming an at least partially continuous annular rim around the circumference of the shell. The graft material may overlay an anterior portion of the shell and may be coupled to the at least partially continuous annular rim with bioabsorbable sutures. Upon implantation, the shell may be partially filled with a filler material until the graft material is gently pressed against a posterior portion of the patient skin flap, promoting its integration.

17 Claims, 14 Drawing Sheets

(56) References Cited

U.S. PATENT DOCUMENTS

| | | | |
|---|---|---|---|
| 2007/0233273 A1 | 10/2007 | Connell | |
| 2009/0125107 A1* | 5/2009 | Maxwell | A61L 27/50 |
| | | | 623/8 |
| 2011/0106249 A1 | 5/2011 | Becker | |
| 2015/0012089 A1* | 1/2015 | Shetty | A61F 2/0059 |
| | | | 623/8 |
| 2015/0025563 A1* | 1/2015 | Mosharrafa | A61B 90/02 |
| | | | 606/191 |
| 2016/0082235 A1* | 3/2016 | Mosharrafa | A61M 29/02 |
| | | | 606/192 |
| 2016/0250016 A1* | 9/2016 | Bertoli | A61F 2/12 |
| | | | 623/8 |
| 2017/0014226 A1 | 1/2017 | Fenaroli | |
| 2018/0280132 A1 | 10/2018 | Shetty et al. | |
| 2018/0333252 A1 | 11/2018 | Ansorge et al. | |

* cited by examiner

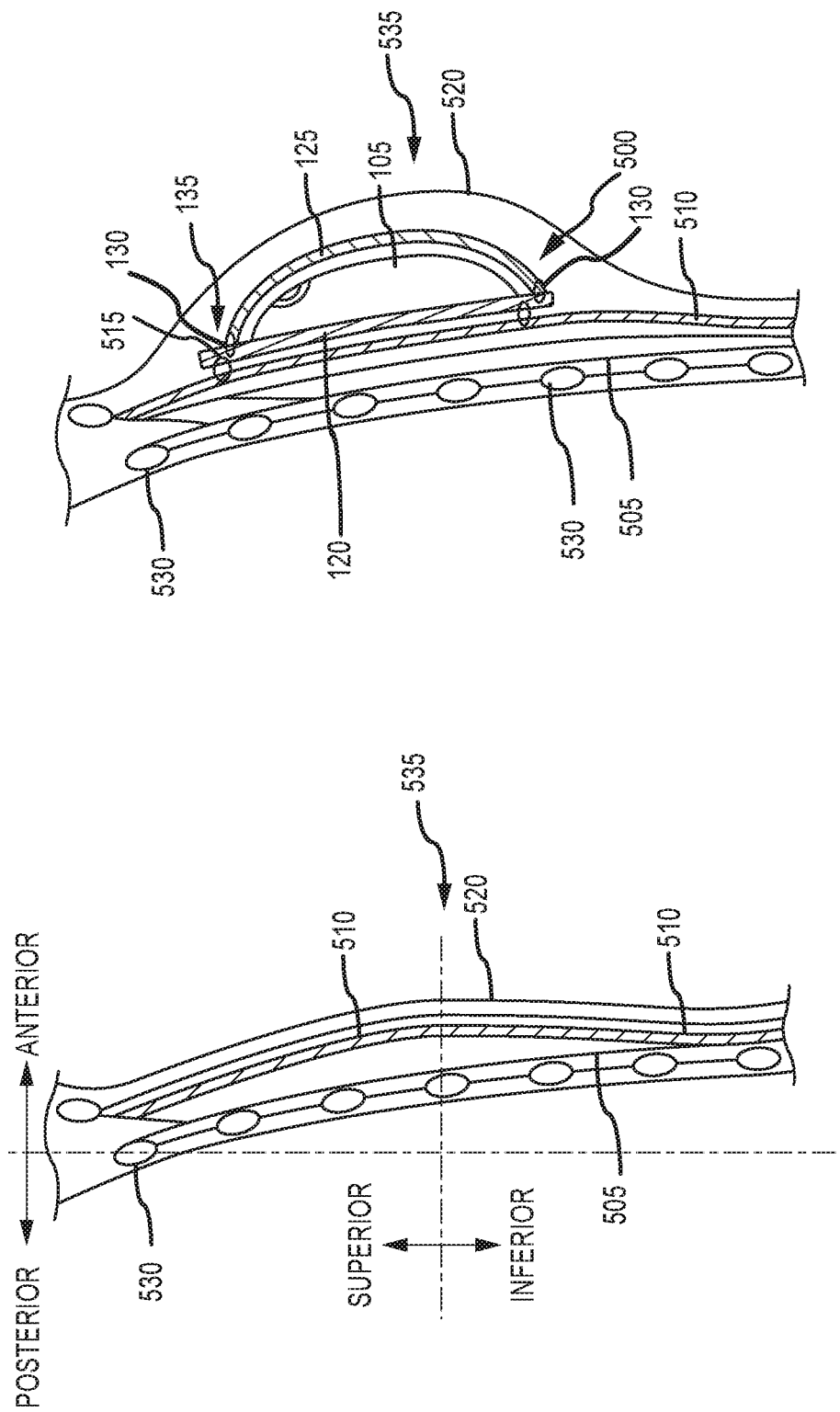

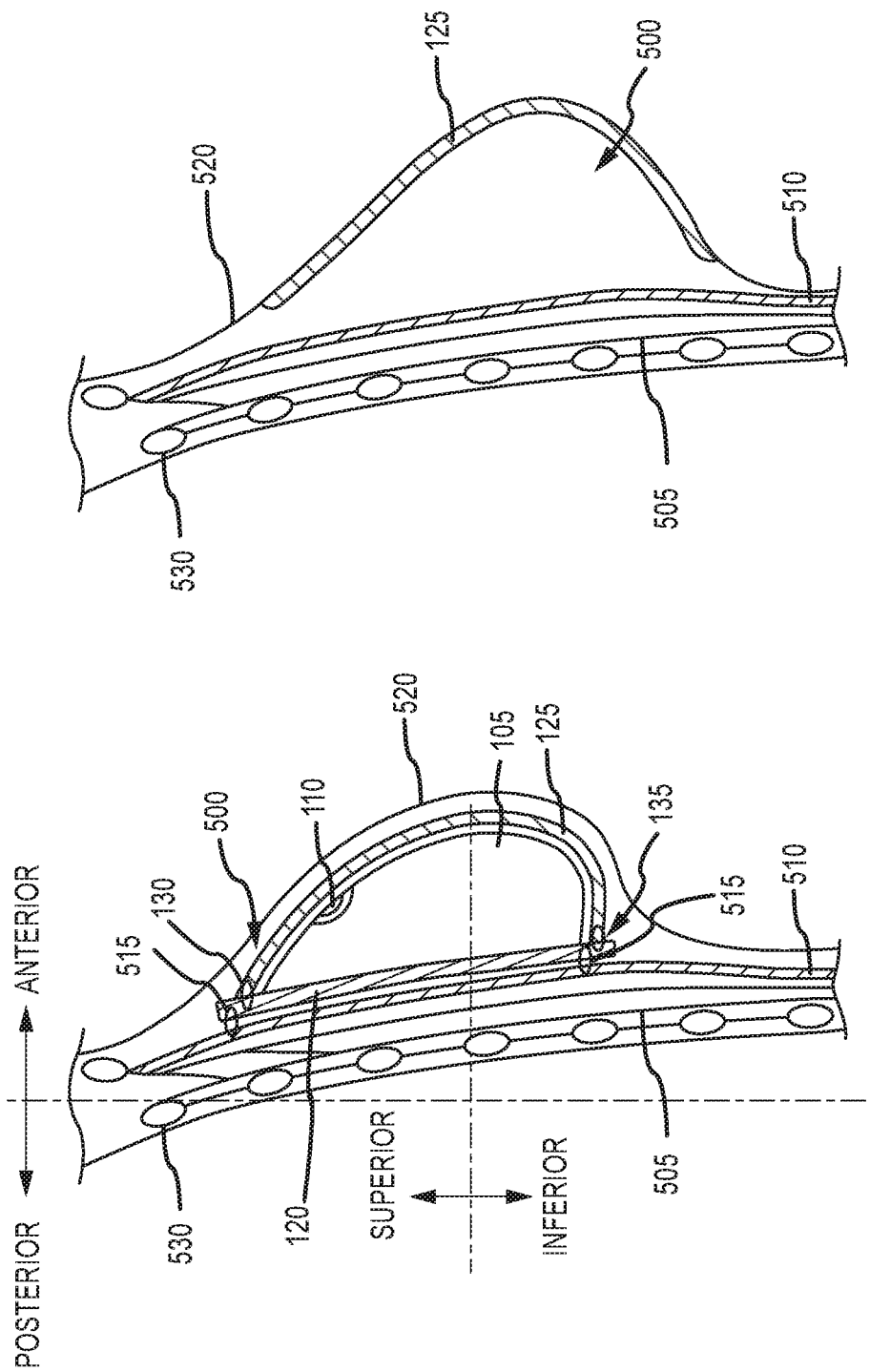

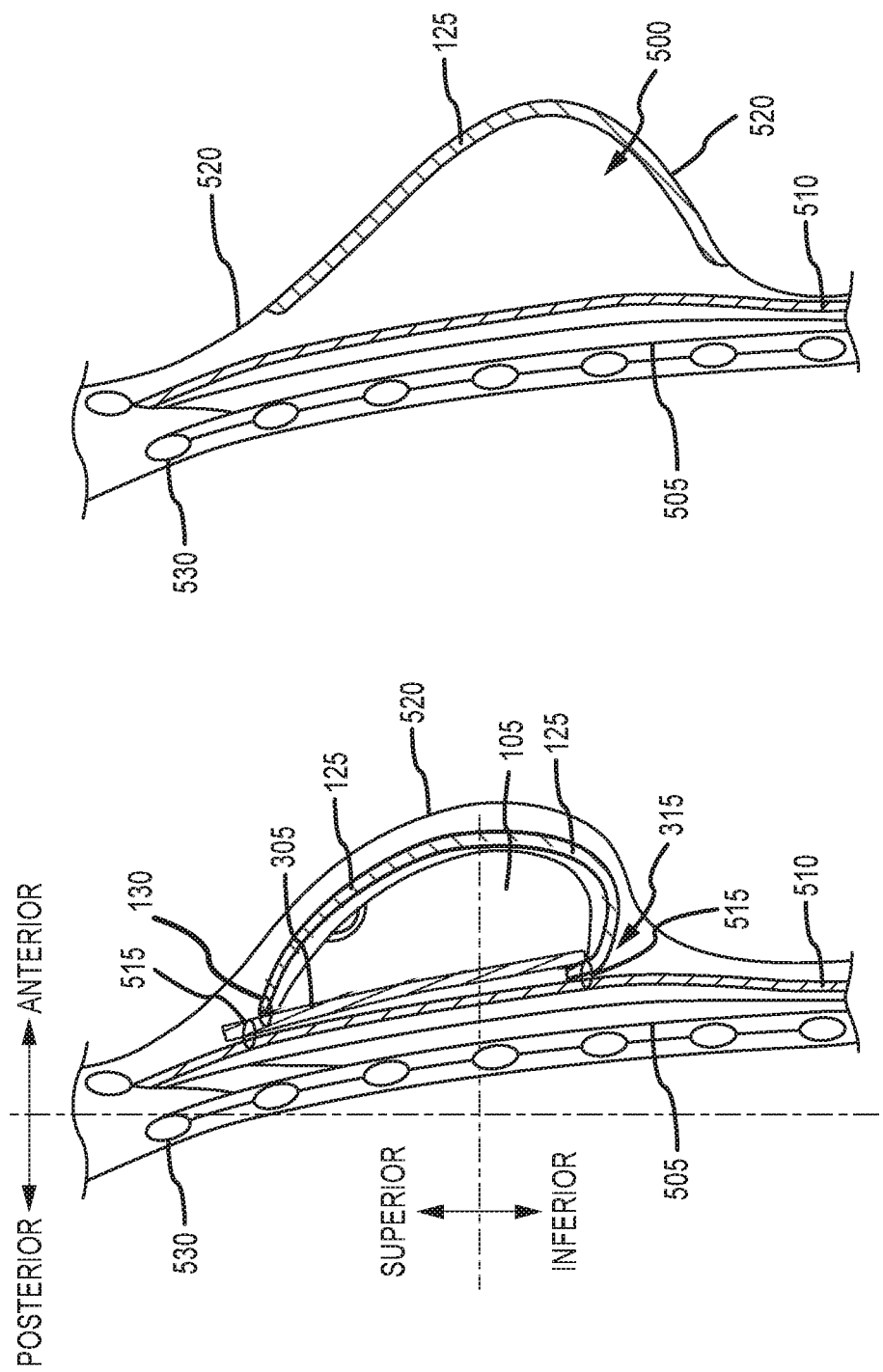

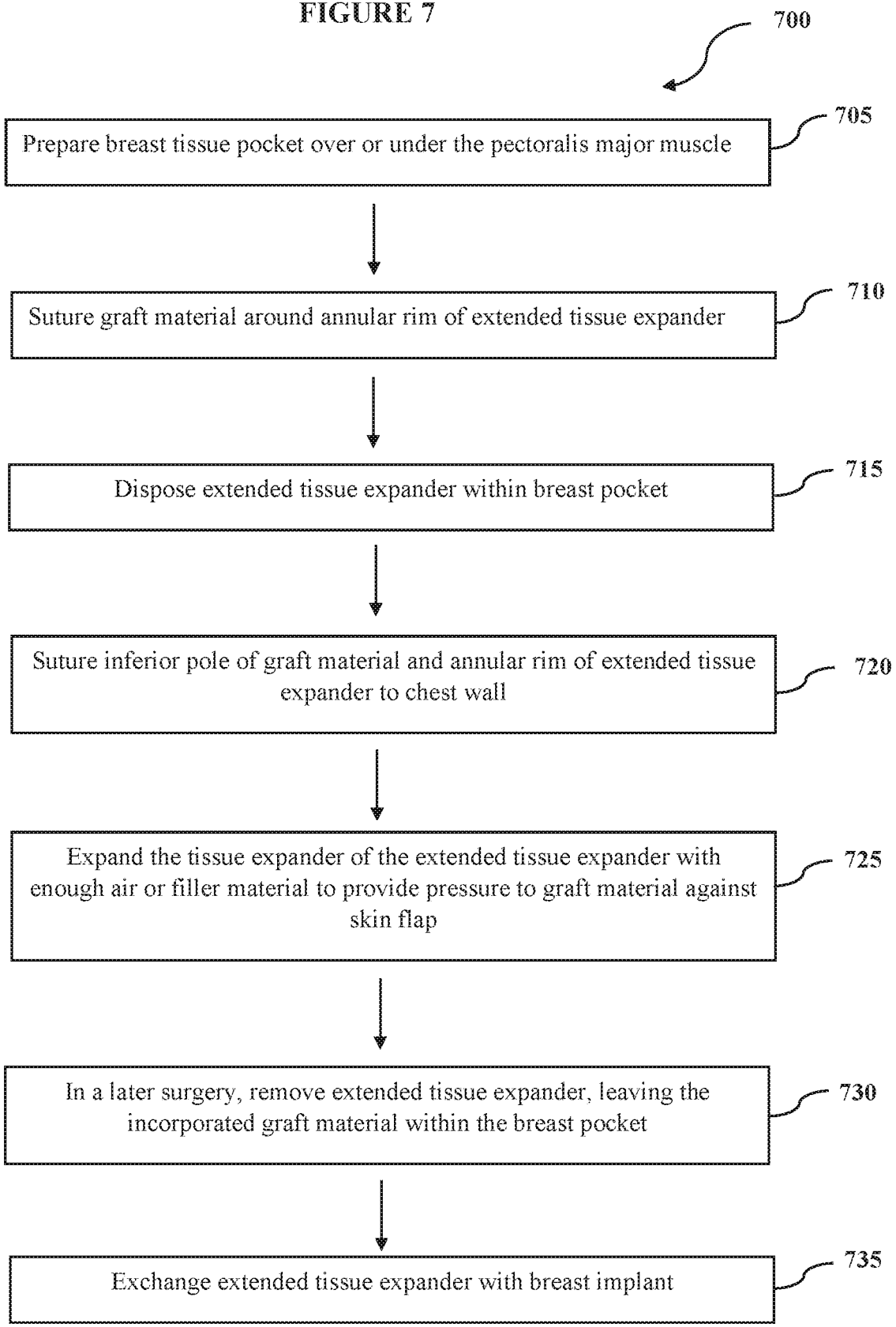

SYSTEMS AND METHODS FOR A TISSUE EXPANDER

CROSS-REFERENCES TO RELATED APPLICATIONS

This application claims the benefit of U.S. Provisional Patent Application No. 62/850,287, filed on May 20, 2019, titled "Breast Tissue Expander with a Perimeter Rim that Allows a Graft to be Sutured Directly to the Expander" and U.S. Provisional Patent Application No. 62/987,301, filed on Mar. 9, 2020, titled "Systems and Methods for a Tissue Expander," and incorporates these disclosures by reference. To the extent that the present disclosure conflicts with any referenced application, however, the present disclosure is to be given priority.

BACKGROUND

Reconstructive surgeries employ soft tissue expansion techniques to create a stretched area of skin for prosthetic implant placement. A conventional tissue expander comprises an expandable balloon placed beneath a patient's skin or muscle that is gradually expanded to achieve a desired expanded tissue pocket. Soft tissue expansion may have advantages over conventional skin grafting for forming the tissue pocket, including providing a natural appearance in skin texture and color by matching the surrounding skin and an existing blood supply.

Tissue expanders may be used for surgical breast reconstruction following a mastectomy. Breast reconstruction involves a multistage process in which the affected breast tissue and skin is removed in a first surgery (mastectomy). A collapsed or partially inflated tissue expander may be placed under or over the pectoralis major muscle behind the area of the removed breast during the first surgery to create a new breast pocket. The tissue expander may be post-operatively filled with a filler material, such as saline or air, over several days, weeks, or even months until the breast pocket achieves a desired volume and shape to accommodate a final permanent breast implant. In a subsequent surgery, the tissue expander may be removed and replaced with the final permanent breast implant, or the breast may be reconstructed with the patient's own tissue with tissue flap surgery.

Current breast tissue expanders comprise a silicone elastomer shell with an injection port for the filler material. Some breast tissue expanders may further include suture tabs for suturing the tissue expander to tissue on the patient's chest wall. The suture tabs, however, are often small and difficult for the surgeon to access during surgery.

Once implanted under or over the pectoralis major muscle during the first-stage surgery, a fibrous capsule of scar tissue forms over the tissue expander as part of a normal physiologic response to a foreign object. This encapsulated breast pocket ultimately receives the final breast implant. The thickness of the capsule may range from thin to heavily-thickened and may exhibit various problems such as capsular contracture, constricting the breast pocket and causing deformation of the breast pocket, excessive firmness of the breast pocket, and/or pain.

Regenerative tissues, also called graft materials, may be used along with tissue expanders to improve healing and optimal formation of the breast pocket. Graft materials such as allogeneic or xenogeneic acellular dermal tissue matrices (ADMs), tissue products from human or mammalian cadavers, or synthetic material grafts may allow the surgeon to fix the position of the breast tissue expander and may also provide a supportive tissue scaffold for implantation over or under the pectoralis major muscle.

Graft materials may be used by suturing the graft material in the breast pocket to create a pocket into which the breast tissue expander is inserted or wrapping the breast tissue expander in a pouch of graft material prior to implantation into the breast pocket. While the use of graft materials may have many benefits, they are also costly and increase the time a patient is in surgery because of the time the surgeon needs to position and suture the graft material into the breast pocket.

BRIEF DESCRIPTION OF THE DRAWINGS

A more complete understanding of the present technology may be derived by referring to the detailed description when considered in connection with the following illustrative figures. In the following figures, like reference numbers refer to similar elements and steps throughout the figures.

Elements and steps in the figures are illustrated for simplicity and clarity and have not necessarily been rendered according to any particular sequence or scale. For example, steps that may be performed concurrently or in different order are illustrated in the figures help to improve understanding of embodiments of the present technology.

Figure 1A:
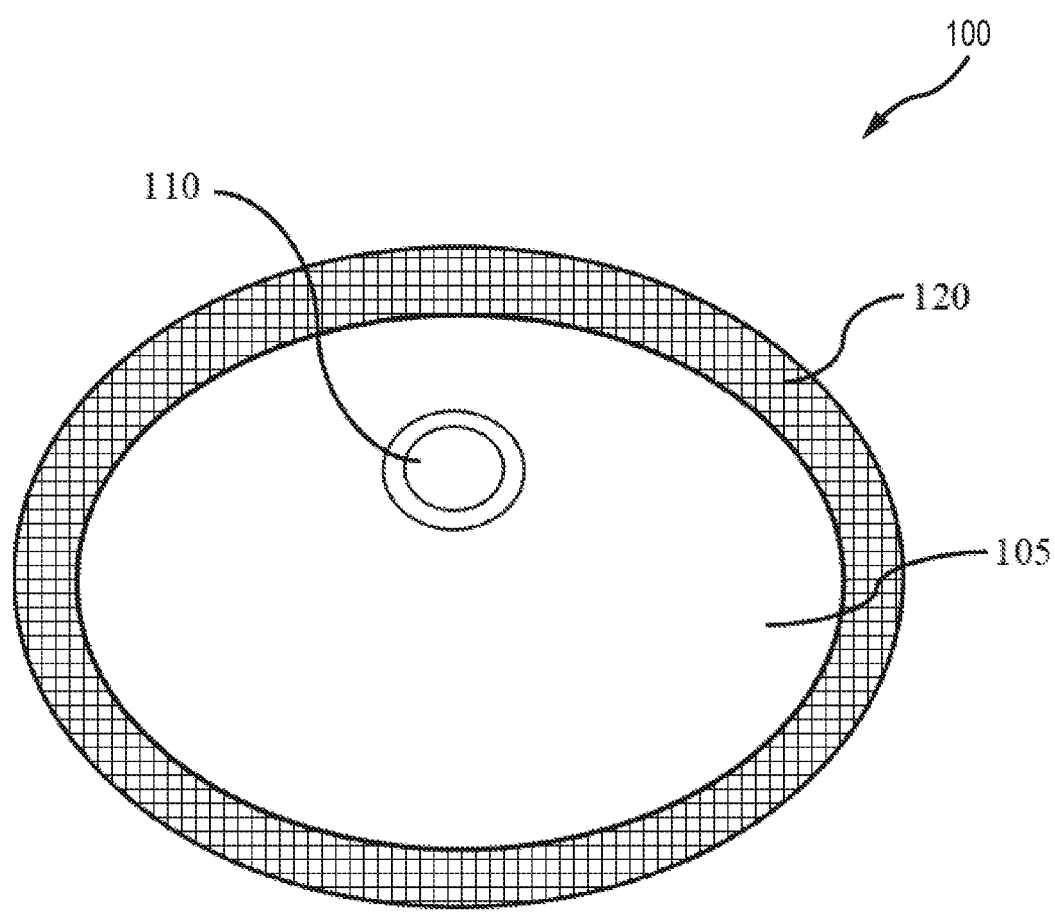
Figure 1B:
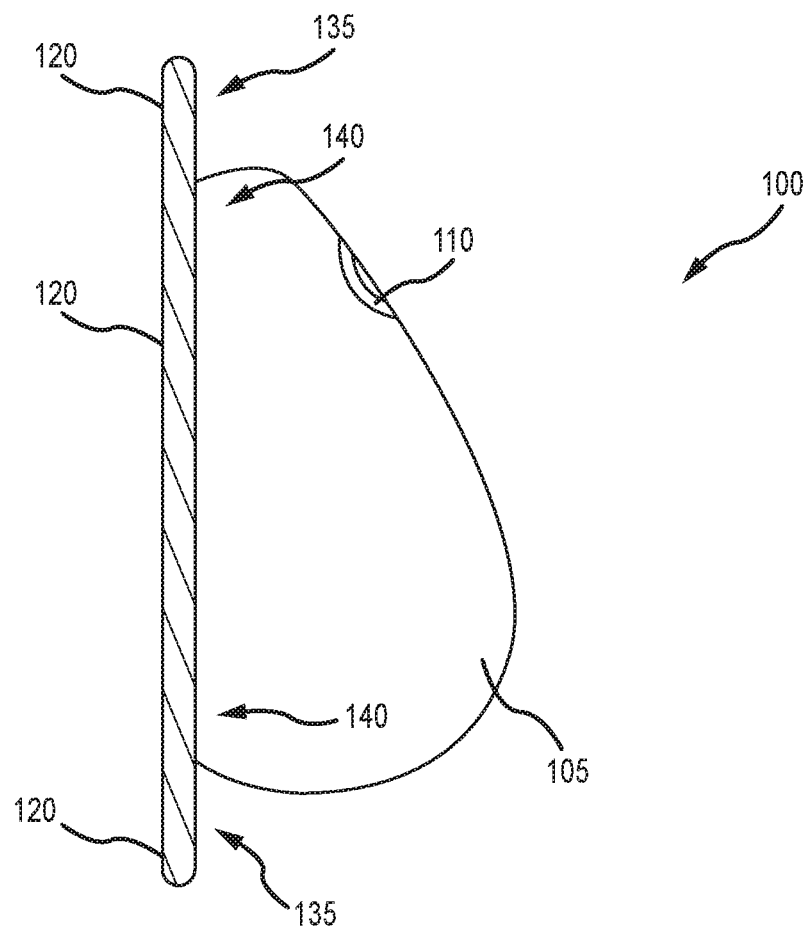
Figure 1C:
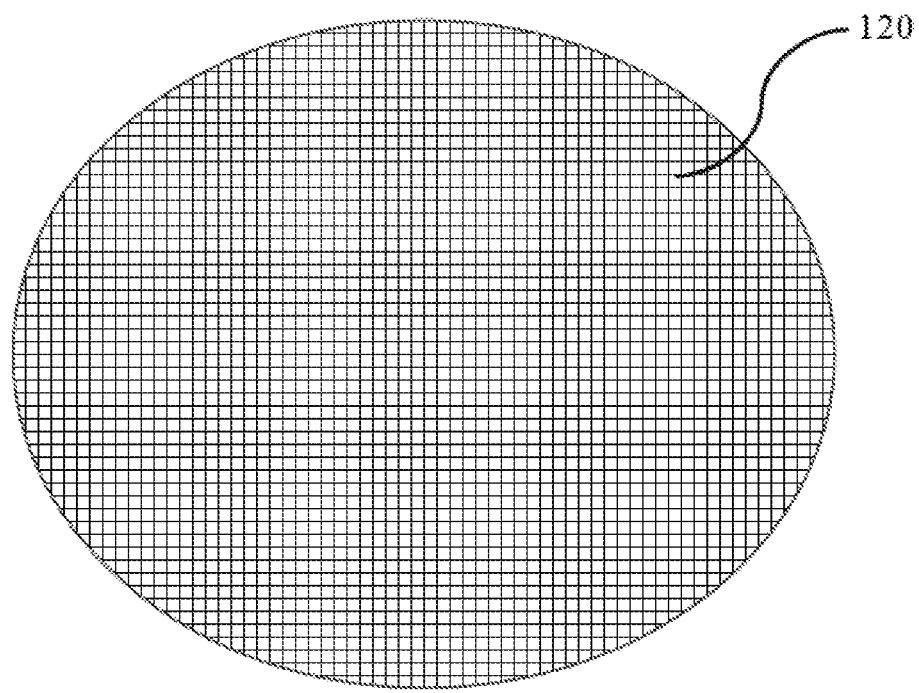
Figure 2A:
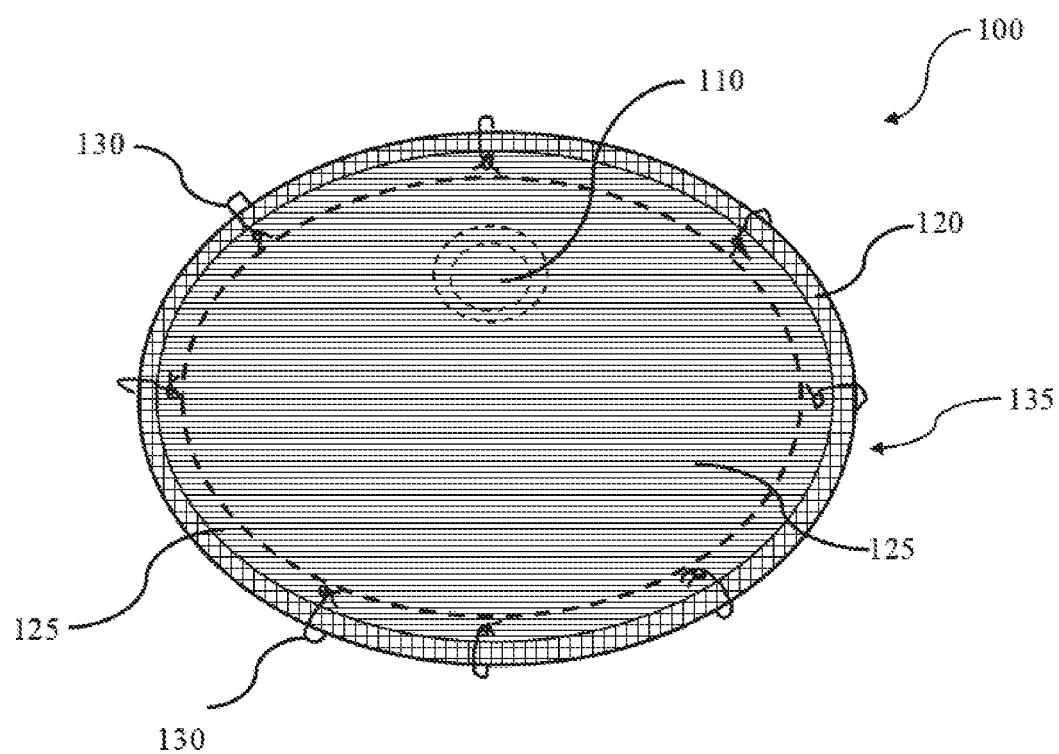
Figure 2B:
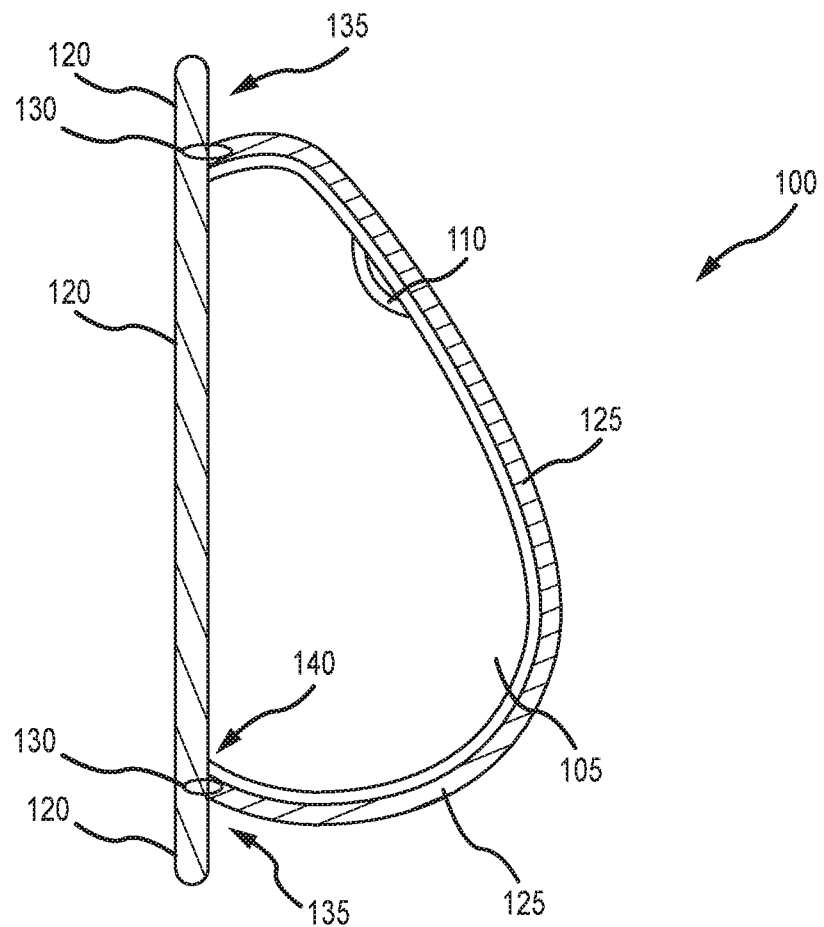
Figure 3A:
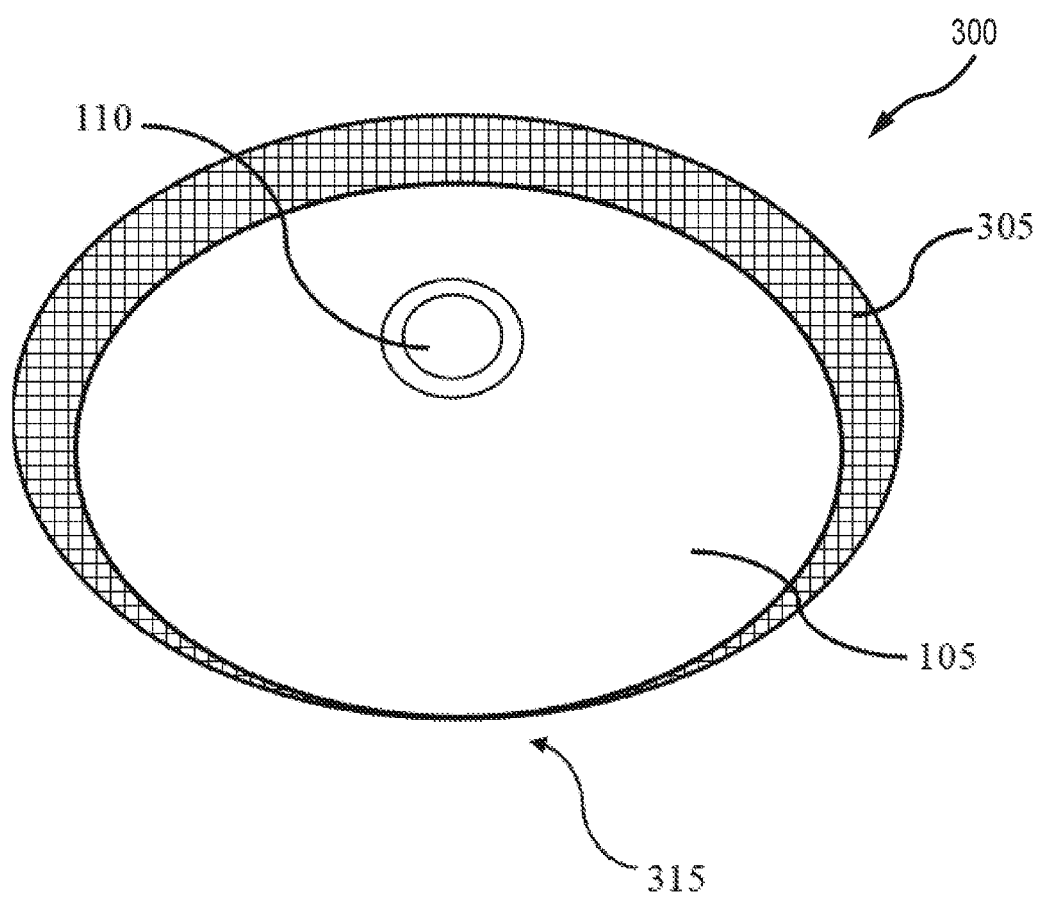
Figure 3B:
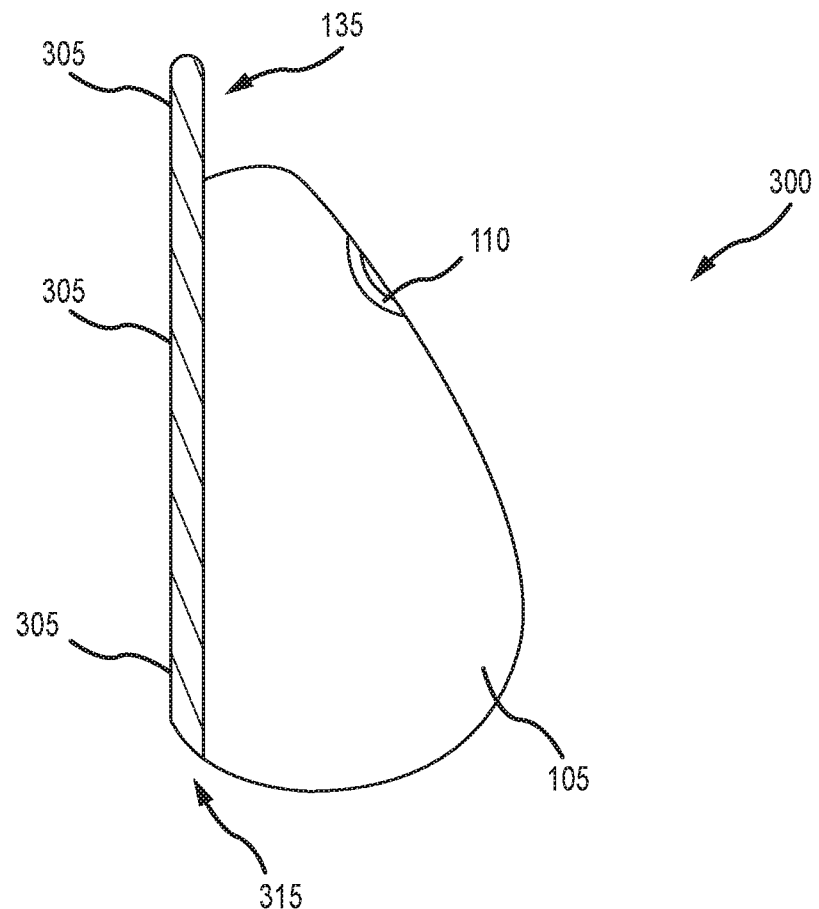
Figure 4A:
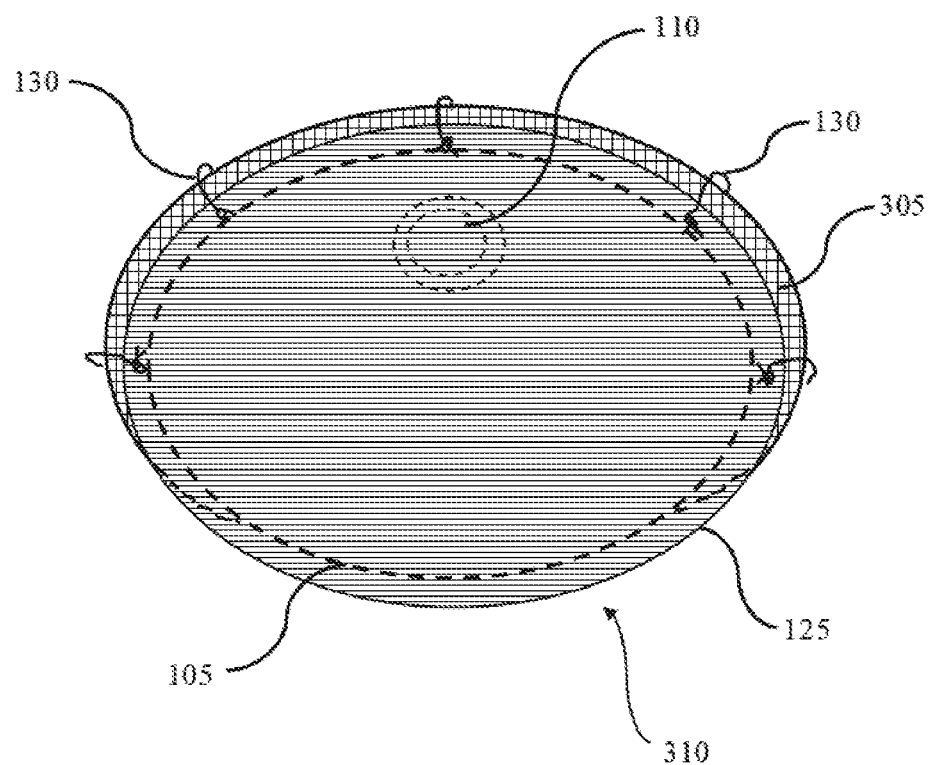
Figure 4B:
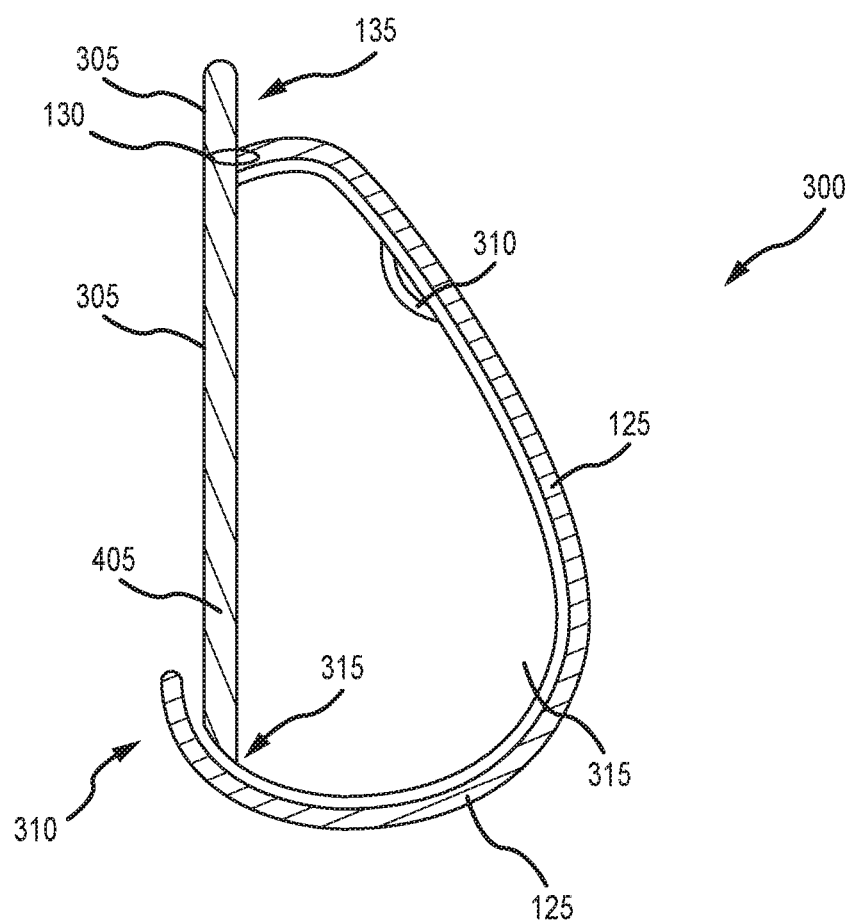

The figures described are for illustration purposes only and are not intended to limit the scope of the present disclosure in any way. Various aspects of the present technology may be more fully understood from the detailed description and the accompanying drawing figures, wherein:

FIGS. 1A-C representatively illustrate anterior, lateral, and posterior views, respectively, of exemplary extended tissue expanders;

FIGS. 2A-2B representatively illustrate anterior and lateral views, respectively, of an exemplary extended tissue expander with graft;

FIGS. 3A-B representatively illustrate anterior and lateral views, respectively, of an alternative embodiment of an exemplary extended tissue expander;

FIGS. 4A-B representatively illustrate anterior and lateral views, respectively, of an alternative embodiment of an exemplary extended tissue expander with graft;

FIGS. 5A-D representatively illustrate lateral views of an extended tissue expander disposed within a breast pocket of a patient;

FIGS. 6A-D representatively illustrate lateral views of an alternative embodiment of the extended tissue expander disposed within a breast pocket of a patient; and FIG. 7 is a flow chart of a method of using an exemplary extended tissue expander.

DETAILED DESCRIPTION OF EXEMPLARY EMBODIMENTS

The present technology may be described herein in terms of functional block components and various processing steps. Such functional blocks may be realized by any number of components configured to perform the specified functions and achieve the various results. For example, methods and systems according to various aspects of the present technology may be practiced in conjunction with any number of systems and methods for tissue reconstruction, tissue expansion, and breast pocket preservation, and the systems described are merely exemplary applications for the present technology. Various representative implementations of the present technology may be applied to any appropriate type of tissue expander.

The particular implementations shown and described are illustrative of the invention and its best mode and are not intended to otherwise limit the scope of the present invention in any way. For the sake of brevity, conventional manufacturing, preparation, sterilization, surgical techniques, and other functional aspects of the system may not be described in detail. Furthermore, the connecting lines shown in the various figures are intended to represent exemplary functional relationships and/or steps between the various elements. Many alternative or additional functional relationships or physical connections may be present in a practical system.

Various aspects of the invention provide methods, apparatus, and systems for making and using an extended tissue expander system, such as for reconstructive surgeries. The present detailed description of various embodiments provides a specific enabling disclosure that may be generalized to any application of the disclosed systems and methods.

Various representative implementations of the present technology may be applied to any appropriate system for tissue reconstruction. Certain representative implementations may include, for example, any suitable system or method for extending the backing on a conventional tissue expander to create a perimeter of suturable material to which a grafting material may be attached. In one embodiment, the extended tissue expander system may comprise a static nonexpandable annular backing comprising an annular rim coupled to a conventional inflatable tissue expander, such as a tissue expander used for facial reconstruction or breast reconstruction following mastectomy.

In one embodiment, the combination of the static extended backing with the conventional tissue expander may maintain established soft tissue expansion methods and techniques, such as for breast tissue expansion, while providing an at least partially continuous suturable annular rim around the extended backing that extends out from the backing of the tissue expander. In some embodiments, the annular rim of the extended backing may be sutured to the patient to prevent rotation of the tissue expander in the breast pocket.

In some embodiments, a graft material may be sutured to the annular rim of the extended backing to cover an anterior portion of the extended tissue expander. The application of the graft material to the extended tissue expander may be particularly useful for creating a breast pocket over the pectoralis major muscle. This type of placement of the extended tissue expander, and ultimately the breast implant, may have advantages over submuscular placement because the shape and projection of the breast pocket may be aesthetically superior and less bleeding may occur during and/or after surgery. However, placement of the extended tissue expander over the pectoralis major muscle results in only having the patient's skin flap over the extended tissue expander. The skin flap may be too thin to provide a stable breast pocket and may result in marked capsular contracture. Use of the graft material over the extended tissue expander such that the graft material is gently pressed against the posterior portion of the skin flap may promote incorporation of the graft into the skin flap for thicker coverage over the extended tissue expander. This thicker coverage may improve stability of the breast pocket and reduced capsular contracture while retaining the advantages of the aesthetically superior shape and projection of the breast pocket that results from supra-muscular placement.

Referring to FIGS. 1A-C, exemplary embodiments of the extended tissue expander 100 may comprise a shell 105 coupled to an extended backing 120, wherein the shell defines a closed interior volume to receive and retain a filler material, such as saline. The extended tissue expander 100 may comprise any suitable system or device for effecting gradual breast tissue and skin expansion or stretching. The shell 105 and the extended backing 120 may be constructed from any suitable surgical grade material such as a silicone elastomer or polypropylene.

The shell 105 may expand anteriorly as the filler material is added to the interior volume through a fill port 110. In some embodiments, the fill port 110 may comprise a septum or other self-sealing integral injection port that may be pierced with a hypodermic needle to introduce the filler material into a lumen of the extended tissue expander 100 for inflation. In other embodiments, the fill port 110 may be located remotely from the extended tissue expander 100. For example, the fill port 110 may be coupled to the extended tissue expander 100 through tubing (not shown) to allow the filler material to flow from the fill port 110 into the lumen of the extended tissue expander 100.

Referring to FIGS. 1A and 1C, the extended backing 120 may comprise a substantially nonexpandable posterior section of the shell with an at least partially continuous annular rim 135 extending therefrom. The extended backing 120 may be a substantially nonexpandable flat sheet that does not appreciably compress or distend as the filler material is added to the interior volume of the shell. In one embodiment as applied to breast reconstruction, the extended backing 120 may provide a substantially flat surface with a firmness that may allow the shell 105 to expand anteriorly away from the chest wall, resulting in a teardrop-shaped tissue pocket that may form a more natural tight shape to receive the final breast implant.

In some embodiments, the extended backing 120 may comprise a different material than the shell 105, wherein the material is substantially nonexpandable. Alternatively, the extended backing 120 may comprise a thicker portion of the same material as the shell 105, and/or the extended backing 120 may be attached to a substantially nonexpandable material to inhibit expansion.

Referring to FIG. 1B, in various embodiments of the present technology, an at least partially continuous annular rim 135 extending from the extended backing 120 may extend beyond a seam 140 joining the shell 105 with the extended backing 120 by any suitable distance that may be suturable. In some embodiments, the annular rim 135 may extend three hundred and sixty degrees around the circumference of the posterior section of the shell 105. In some embodiments, the annular rim 135 may be up to approximately three (3) centimeters wide to provide enough material to apply a stitch.

Referring to FIGS. 3A-B, in some embodiments, the inferior pole 315 of annular rim 135 may be absent or shorter than the annular rim 305 around the rest of the extended tissue expander 300. For example, in one embodiment, the annular rim 305 may be absent from approximately twenty percent (20%) to approximately forty percent (40%) of the circumference of the posterior section of the shell 105. The absent or shorter annular rim 305 may provide an area for stitching a graft material to the chest wall just under the inferior pole of the extended tissue expander 100.

Referring to FIGS. 2A-B, the extended tissue expander 100 may be coupled to a graft material 125. The graft material 125 may comprise any suitable biocompatible material that incorporates into the patient's own tissue to serve as a scaffold for the patient's cells to facilitate incorporation and revascularization. In various embodiments, the graft material 125 may comprise decellularized tissue (ex., acellular dermal matrix or "ADM"), synthetic tissue, and/or processed tissue.

The graft material 125 may be coupled to the annular rim 135 of the extended tissue expander 100, such that the graft material 125 overlays the anterior face of the shell 105. In some embodiments, little to no portion of the graft material 125 may be behind the extended backing 120, which may reduce the amount of graft material 125 that has to be used and may reduce costs. The graft material 125 may function to promote proper healing and formation of the breast pocket and may also prevent formation of a contractile pseudocapsule around the extended tissue expander 100.

In various embodiments, the graft material 125 may be coupled to the annular rim 135 by any suitable fastener, such as a suture 130. The graft material 125 may be sutured to the annular rim 135 with a bioabsorbable suture placed through the graft material 125 and at least one of a superior, lateral, medial, and inferior portion of the annular rim as chosen by the surgeon placing the extended tissue expander 100 in a patient's breast pocket. As shown in the embodiment of FIG. 2A, the graft material 125 may be sutured to the continuous annular rim 135 at multiple points around the entire annular rim 135.

Referring to FIGS. 4A and 4B, the graft may be coupled to at least one of the superior, lateral, and medial portions of an annular rim 305 with sutures 130. Since the inferior portion 315 of the annular rim 305 is absent in this embodiment, the lower portion 310 of the graft material 125 may not be secured to the extension portion 120 or the annular rim 305. Upon implantation, the lower portion 310 of the graft material 125 may be sutured to the patient's underlying muscle fascia, such as the pectoralis major and/or the rectus abdominus muscle fascia, and/or the chest wall fascia depending on the patient's own muscle boundaries.

Referring to FIGS. 5A-D, an exemplary method of using the present technology is shown. In this method, the extended tissue expander 100 comprises a continuous annular rim 135 that extends around the whole circumference of the posterior section of the shell 105. A breast pocket 500 may be formed and/or maintained in conjunction with the extended tissue expander 100. The surgeon may initially form the initial breast pocket 500 in conjunction with conventional techniques. The surgeon may also prepare the extended tissue expander 100, for example by selecting the appropriately sized extended tissue expander 100. The surgeon may also fold the extension portion 125 to initially fit into the breast pocket 500, and then release and/or adjust the extension portion 125 so that the resilience of the extension portion 125 allows the extension portion 125 to resume its form.

In various embodiments, the extended tissue expander 100 may be disposed into the breast pocket 500, wherein the breast pocket 500 is located in any suitable anatomic soft tissue plane in the breast area 535 (FIG. 5B). In one embodiment, the extended tissue expander 100 may be implanted over the pectoralis major muscle 510, which lays anteriorly to the chest wall 505 and the ribs 530. In another embodiment, the extended tissue expander 100 may be implanted subcutaneously anteriorly to the pectoralis major muscle 510. In other embodiments, the extended tissue expander 100 may be implanted under the pectoralis major muscle 510 or under other muscles in the chest wall 505, such as the pectoralis minor, serratus anterior, or the latissimus dorsi (not shown).

For example, the extended tissue expander 100 may be implanted subcutaneously into the patient during the first surgery of the two-stage breast reconstruction. An exemplary first surgery of a two-stage breast reconstruction surgery may be performed upon a breast area 535, for example where cancer-affected breast tissue and skin has been removed by mastectomy (FIG. 5A). An exemplary extended tissue expander 100 comprising a graft material 125 coupled to the annular rim 135 may be implanted into the breast pocket 500 created by the surgeon (FIG. 5B). In one embodiment, the shell 105 of the extended tissue expander 100 may be at least partially collapsed upon implantation during the first surgery. Accordingly, the breast pocket 500 is not yet formed to the desired volume needed for the final breast implant.

In some embodiments, the extended tissue expander 100 may be used to expand the breast pocket in preparation for the second surgery in which the patient receives a tissue flap for breast reconstruction instead of the final breast implant (not shown). In a tissue flap surgery, the patient's own skin, fat, and/or muscle from another part of their body may be removed for use in reconstructing the breast or gradually moved to the breast area without severing the flap's blood supply. In one embodiment, the tissue flap may comprise skin and tissue taken from another part of the patient's body for use in reconstruction of the breast, such as a deep inferior epigastric artery perforator (DIEP) flap, a superior gluteal artery perforator (SGAP) flap, or an inferior gluteal artery perforator (IGAP) flap. In another embodiment, the tissue flap may comprise muscle in addition to skin and tissue taken from another part of the patient's body, such as a transverse rectus abdominus muscle (TRAM) flap.

In one embodiment, the extended tissue expander 100 coupled to the graft 125 may be disposed within the breast pocket 500 with the shell 105 at least partially collapsed (FIG. 5B). The annular rim 135 may be sutured to the underlying muscle fascia and/or chest wall fascia to secure and stabilize the position of the extended tissue expander 100 in the breast pocket 500, minimizing or preventing shifting and rotation of the extended tissue expander 100. The shell 105 may be filled with filler material sufficient to gently press the graft material 125 onto the posterior face of the skin 520 (FIG. 5B). This connection between the graft material 125 and the skin 520 at the time of implantation encourages immediate incorporation of the graft material 125 into the skin 520. The integration of the graft material 120 into the skin 520 in the shape of the shell 105 provides a stronger and optimally formed and shaped breast pocket 500, as shown in FIG. 5C, at the second surgery when the extended tissue expander is removed, leaving behind the graft material 120, and implantation of the final breast implant (FIG. 5D).

In one embodiment, the shell 105 may be filled with filler material during and/or after surgery to gradually expand the shell 105 over time until the breast pocket 500 reaches a desired volume to accommodate the final breast implant. The extended tissue expander 100 may then be exchanged with the final breast implant without further surgical modification of the breast pocket 500, for example in conjunction with a second surgery of the two-stage breast reconstruction.

Figure 6B:
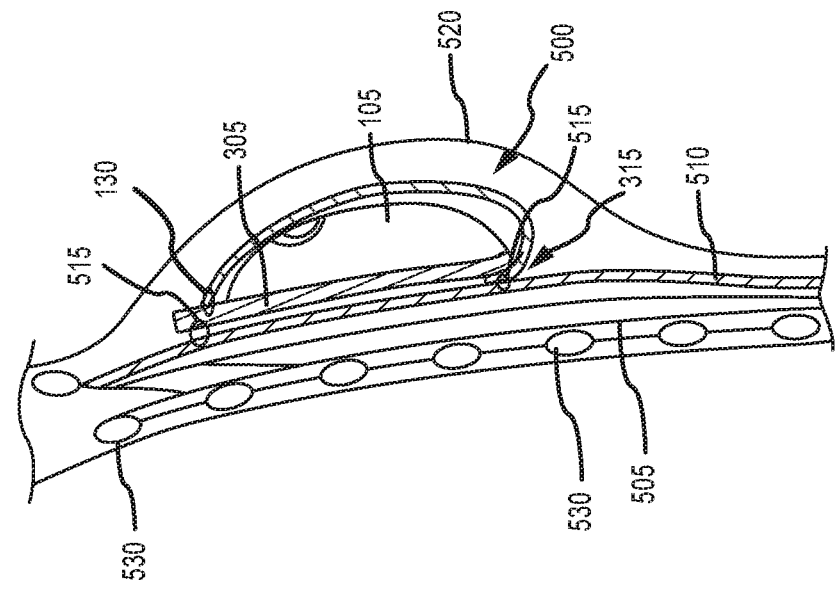
Figure 6A:
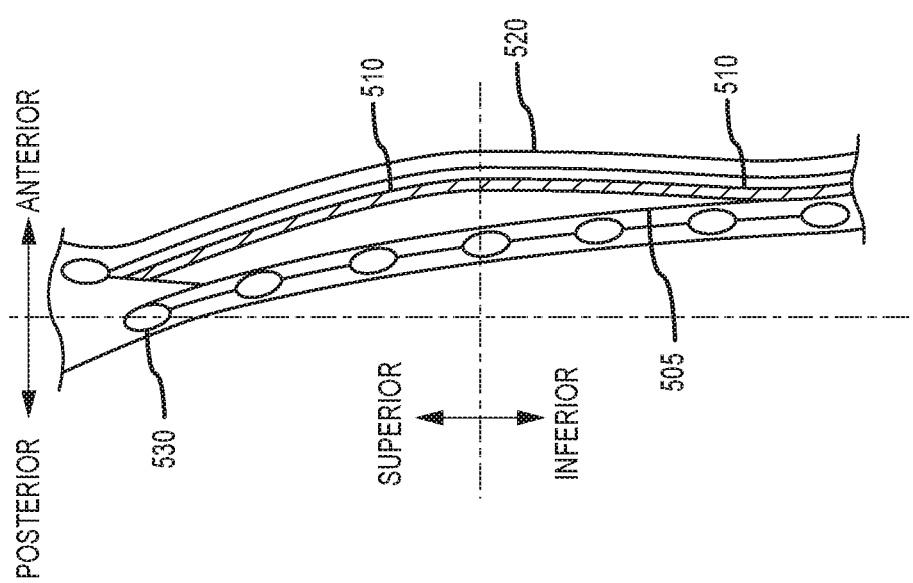

Referring to FIGS. 6A-D, implantation of the extended tissue expander 400 comprising an annular ring 305 that is missing the inferior portion 315 is illustrated. FIG. 6A shows the same preparation of the breast pocket 500 after mastectomy as FIG. 5A. The graft material 125 may be coupled to at least one of the superior, lateral, and medial portions of an annular rim 305. The annular rim 305 may be sutured with sutures 515 to the underlying muscle fascia and/or chest wall fascia to secure and stabilize the position of the extended tissue expander 100 in the breast pocket 500, minimizing or preventing shifting and rotation of the extended tissue expander 100.

The lower portion 310 of the graft material 125 may be wrapped under the shell 105 and tucked behind the inferior portion 315 of the annular rim 305 (FIG. 6B). Sutures 515 may be placed in the lower portion 310 of the graft material 125 to secure the graft material 125 to the patient's underlying muscle fascia 510 and/or the chest wall fascia 505 that is behind the inferior portion 315 of the annular rim 305. The graft material 125 tucked under the shell 105 in this manner may create a sling for the shell 105 to rest in as it settles and expands, which may provide a more natural shape to the breast pocket 500.

Referring to FIG. 6C-D, the shell 105 may be filled with filler material sufficient to gently press the graft material 125 onto the posterior face of the skin 520 to facilitate incorporation of the graft material 125 into the skin 520 (FIG. 6C). At the second surgery when the extended tissue expander 100 is removed, the graft material 125 remains incorporation into the skin 520 and implantation of the final breast implant may occur (FIG. 6D).

Referring to FIG. 7, an exemplary method 700 of using the extended tissue expander 100 with the graft material 125 may include preparing the breast pocket over or under the pectoralis major muscle (705). The graft material 125 may be temporarily coupled to the annular rim 135 of the extended tissue expander 100 with any suitable temporary bioabsorbable material, such as a bioabsorbable suture (710). For example, the bioabsorbable suture may comprise a material that absorbs within approximately three (3) months after it is placed in the body, such as Vicryl sutures. In various embodiments, the graft material 125 may be sutured at multiple points 360° around the annular rim 135 of the extended tissue expander 100. In some embodiments, the lower portion 315 of the annular rim 305 may be absent and the graft material 125 may be sutured to the annular rim 305 on at least its superior, lateral, and medial portions.

The extended tissue expander 100 with the attached graft material 125 may be disposed within the breast pocket (715). In some embodiments, the lower portion 310 of the graft material 125 may be sutured to the chest wall (720). Attachment of the lower portion 310 of the graft material 125 to the chest wall may create a cuff or sling that may support the lower pole of the extended tissue expander as it settles in the breast pocket with gravity. In some embodiments, the annular rim 135 of the extended tissue expander 100 may be sutured to the chest wall (720). For example, at least one of the medial, lateral, superior, and inferior portions of the annular rim 135 may be sutured to the chest wall to prevent rotation of the extended tissue expander 100. The extended tissue expander 100 disposed within the breast pocket may be expanded with enough air and/or filler material to provide pressure to the graft material 125 against the skin flap (725). In some embodiments, an anterior face of the graft material 125 may be sutured to the patient's skin flap, such as in nipple sparing mastectomy where the position of the nipple needs to be maintained over the course of tissue expansion. After suturing has been completed, the surgery may be concluded.

The extended tissue expander 100 with the attached graft material 125 within the closed breast pocket 500 may be periodically filled with filler material to expand the breast pocket to the desired size. In a subsequent surgery, the extended tissue expander 100 may be removed from the breast pocket, leaving the incorporated graft material 125 within the breast pocket (730). In various embodiments, the subsequent surgery may typically occur between approximately six (6) weeks to one year after the first surgery in which the extended tissue expander 100 coupled to the graft material 125 was implanted. A breast implant may then be inserted into the breast pocket (735).

In the foregoing description, the technology has been described with reference to specific exemplary embodiments. Various modifications and changes may be made, however, without departing from the scope of the present technology as set forth. The description is to be regarded in an illustrative manner, rather than a restrictive one and all such modifications are intended to be included within the scope of the present technology. Accordingly, the scope of the technology should be determined by the generic embodiments described and their legal equivalents rather than by merely the specific examples described above. For example, the steps recited in any method or process embodiment may be executed in any appropriate order and are not limited to the explicit order presented in the specific examples. Additionally, the components and/or elements recited in any system embodiment may be combined in a variety of permutations to produce substantially the same result as the present technology and are accordingly not limited to the specific configuration recited in the specific examples.

Benefits, other advantages and solutions to problems have been described above with regard to particular embodiments. Any benefit, advantage, solution to problems or any element that may cause any particular benefit, advantage or solution to occur or to become more pronounced, however, is not to be construed as a critical, required or essential feature or component.

The terms "comprises", "comprising", or any variation thereof, are intended to reference a non-exclusive inclusion, such that a process, method, article, composition or apparatus that comprises a list of elements does not include only those elements recited, but may also include other elements not expressly listed or inherent to such process, method, article, composition or apparatus. Other combinations and/or modifications of the above-described structures, arrangements, applications, proportions, elements, materials or components used in the practice of the present technology, in addition to those not specifically recited, may be varied or otherwise particularly adapted to specific environments, manufacturing specifications, design parameters or other operating requirements without departing from the general principles of the same.

The present technology has been described above with reference to an exemplary embodiment. However, changes and modifications may be made to the exemplary embodiment without departing from the scope of the present technology. These and other changes or modifications are intended to be included within the scope of the present technology.

What is claimed is:

1. An extended tissue expander for filling with a filler material and implantation in the breast area of a patient, comprising:
   a breast tissue expander, comprising:
      a shell defining a closed interior volume configured to retain the filler material, wherein the shell comprises:
         an expandable anterior shell; and
         a substantially nonexpandable posterior section, wherein the posterior section comprises an integrated portion of the shell; and a port disposed through the shell and into the interior volume; and an extension portion coupled to the breast tissue expander, wherein the extension portion:
is integral to the posterior section of the shell, extending therefrom as a partially continuous annular rim, wherein the annular rim is absent from only approximately twenty percent to approximately forty percent of an inferior pole of the shell such that at least one of a medial and a lateral portion of the extension portion is present below a horizontal midline of the shell;
has a substantially uniform thickness;
is substantially nonexpandable to provide a backing to the shell such that the shell expands anteriorly away from the chest wall upon filling with filler material; and
is configured to be sutured.

2. The extended tissue expander of claim 1, wherein the extension portion comprises a single piece of silicone.

3. The extended tissue expander of claim 2, wherein the extension portion further comprises a reinforcement material embedded into the single piece of silicone, enhancing the resilience of the silicone.

4. The extended tissue expander of claim 3, wherein the reinforcement material is a suturable surgical fabric.

5. The extended tissue expander of claim 1, wherein the partially continuous annular rim is up to approximately three centimeters wide.

6. The extended tissue expander of claim 1, further comprising a graft material coupled to the partially continuous annular rim, wherein the graft material overlays an anterior portion of the shell.

7. The extended tissue expander of claim 6, wherein the graft material is sutured to the partially continuous annular rim with a bioabsorbable suture placed through the graft and at least one of a superior, lateral, and medial portion of the partially continuous annular rim.

8. The extended tissue expander of claim 6, wherein the graft material overlays the anterior portion of the shell to contact and integrate into a posterior portion of a skin flap of the patient.

9. A method for forming a final encapsulated breast pocket with a graft material integrated into a posterior portion of a patient's skin flap, comprising:
forming an initial breast pocket in a breast area of the patient;
inserting an extended breast tissue expander into the initial breast pocket, comprising:
a breast tissue expander, comprising:
a shell defining a closed interior volume configured to retain a filler material, wherein the shell comprises:
an expandable anterior shell; and a substantially nonexpandable posterior section, wherein the posterior section comprises an integrated portion of the shell; and
a port disposed through the shell and into the interior volume;
an extension portion coupled to the breast tissue expander, wherein the extension portion:
is integral to the posterior section of the shell, extending therefrom as a partially continuous annular rim, wherein the partially continuous annular rim is absent from only approximately twenty percent to approximately forty percent of an inferior pole of the shell such that at least one of a medial and a lateral portion of the extension portion is present below a horizontal midline of the shell;
has a substantially uniform thickness;
is substantially nonexpandable to provide a backing to the shell such that
the shell expands anteriorly away from the chest wall upon filling with the filler material; and
is configured to be sutured; and
a graft material coupled to the partially continuous annular rim, wherein the graft material overlays an anterior portion of the shell to contact and integrate into a the posterior portion of the skin flap;
suturing the partially continuous annular rim to at least one of an underlying muscle fascia and a chest wall fascia of the patient; and
at least partially inflating the shell with the filler material to press the graft material against the posterior portion of the skin flap.

10. The method of claim 9, wherein the graft material is sutured to the partially continuous annular rim with a bioabsorbable suture placed through the graft and at least one of a superior, lateral, medial, and inferior portion of the partially continuous annular rim.

11. The method of claim 9, further comprising tucking a lower portion of the graft material under the shell and behind the partially continuous annular rim and suturing the graft material to at least one of the patient's underlying muscle fascia and chest wall fascia to create a sling for the shell to rest in.

12. The method of claim 9, wherein the at least partially continuous annular rim is up to approximately three centimeters wide.

13. The method of claim 9, wherein the extension portion comprises silicon with an embedded reinforcement material configured to enhance the resilience of the silicone.

14. The method of claim 13, wherein the reinforcement material is a suturable surgical fabric.

15. The method of claim 9, wherein the initial breast pocket is subcutaneous.

16. The method of claim 15, further comprising suturing an anterior face of the graft material to the posterior portion of the skin flap overlaying the initial breast pocket to maintain the position of a nipple.

17. The method of claim 9, wherein the initial breast pocket is submuscular.

* * * * *